(12) United States Patent
Xia

(10) Patent No.: US 8,639,066 B2
(45) Date of Patent: Jan. 28, 2014

(54) NANO-STRUCTURED TRAMPOLINE FIBER GAS SENSOR

(75) Inventor: Hua Xia, Altamont, NY (US)

(73) Assignee: General Electric Company, Niskayuna, NY (US)

( * ) Notice: Subject to any disclaimer, the term of this patent is extended or adjusted under 35 U.S.C. 154(b) by 76 days.

(21) Appl. No.: 13/307,208

(22) Filed: Nov. 30, 2011

(65) Prior Publication Data

US 2013/0084037 A1    Apr. 4, 2013

Related U.S. Application Data

(60) Provisional application No. 61/540,600, filed on Sep. 29, 2011.

(51) Int. Cl.
*G02B 6/34* (2006.01)
(52) U.S. Cl.
USPC .................. 385/12; 385/13; 385/15; 385/31; 385/37; 385/39
(58) Field of Classification Search
USPC ..................................... 385/12, 37
See application file for complete search history.

(56) References Cited

U.S. PATENT DOCUMENTS

| | | | |
|---|---|---|---|
| 7,151,872 B1* | 12/2006 | Xia et al. | ........................ 385/37 |
| 7,400,789 B2 | 7/2008 | Xia et al. | |
| 7,489,835 B1 | 2/2009 | Xia et al. | |
| 2011/0211795 A1 | 9/2011 | Xia | |
| 2012/0103066 A1* | 5/2012 | Xia et al. | ..................... 73/25.05 |

* cited by examiner

*Primary Examiner* — Ryan Lepisto
(74) *Attorney, Agent, or Firm* — Andrew J. Caruso

(57) ABSTRACT

A fiber gas sensor including a core fiber comprising at least one Bragg grating region, a fiber cladding in contact with the core fiber along an entire length of the core fiber, and a sensing matrix structure disposed upon the outer surface of the fiber cladding along a portion of the length of the fiber cladding and surrounding the fiber Bragg grating region. The sensing matrix structure comprising a bonding layer disposed on the outer surface of the fiber cladding layer, a nano-structured trampoline matrix layer disposed on the outer surface of the bonding layer and a capping layer disposed on the outer surface of the matrix layer. The thermally modulated response amplitude of the fiber gas sensor is found to linearly depend upon the gas molecular weight, and can be directly used to determine heat specific capacity ratio of Cp/Cv.

19 Claims, 8 Drawing Sheets

NANO-STRUCTURED TRAMPOLINE FIBER GAS SENSOR

CROSS-REFERENCE TO RELATED APPLICATIONS

This application is a non-provisional application that claims priority to provisional U.S. Patent Application Ser. No. 61/540,600 filed on Sep. 29, 2011; the disclosure of which is hereby incorporated by reference.

BACKGROUND

The invention relates generally to a fiber optic gas sensor, and more particularly to a nano-structured trampoline integrated fiber Bragg grating sensing device for gas molecular weight detection.

Fiber optic sensors are widely used in the oil and gas industry for monitoring down-hole and turbomachinery parameters such as pressure, temperature, gas composition, hydrocarbon flow and seismic status. Monitoring of such machine operation parameters or/and operation conditions may provide real-time control and optimization for production output and enable condition-based maintenance for prolonging a machine's lifetime. In general, simultaneously measuring both temperature and pressure can be practically done with conventional pressure gauges and thermocouples. Gas composition analysis is commonly based on gas chromatography (GC), micro gas chromatography (MGC), or a mass spectroscopy. More specifically, gas composition analysis is typically based on either laser spectroscopy by analyzing molecular vibration modes, laser and photo-acoustic absorption at specific wavelengths, or on gas chromatography by separating the components of a gas mixture primarily based on boiling point (or vapor pressure) differences.

In many instances, online gas composition and molecular mass analyses are required either for efficiency control or for machine operation control. However, using GC or laser absorption instrument online for monitoring an industrial process, such as analyzing a gas mixture, including multiple gas compositions, is challenging due to time-consuming and complicated instrument field calibration. In one case, the gas analysis requires knowing each composition variation such as in gas fuel quality monitoring; in other case, the gas analysis is for measuring effective gas molecular weight, the ratio Cp/Cv of the constant-pressure specific heat over the constant-volume specific heat, and gas heating value variation, such as in gas charge compressor or compressor train for ethylene production process monitoring. Although, gas characteristics, such as gas molecular weight, are desired to be known, they are not easily determinable and a standard design with nominal value is used for compressor efficiency prediction and control.

Fiber Bragg Grating (FBG) sensors are well known in the art for monitoring the various parameters and machine operations previously noted. More specifically, FBGs are more commonly used to measure temperature, pressure, flow, vibration, strain, and displacement, etc. One advantage is that FBGs can be wavelength multiplexed along one fiber, making them attractive for multi-point measurements or multi-measured measurements. A lesser known application is to use a FBG sensor for gas composition, purity, cleanness, and molecular mass analyses. The technical barrier for using FBG for measuring gas is due mainly to the chemical inactive nature of the silicon dioxide fiber material.

As disclosed in U.S. Pat. No. 7,489,835, U.S. Patent No. 7,400,789 and U.S. Pat. No. 7,489,835 fiber Bragg gratings, integrated with a gas sensitive sensing material layer, have shown measurable wavelength shifts induced by fiber cladding refractive index variation of the sensing layer that interacts with gas molecular. However, these sensors are designed for identifying a specific gas and, more preferred to be used for specific single-component gas analysis. The gas induced sensing layer refractive index change is calibrated with gas concentration. However, it is difficult to analyze a gas mixture that has multi-component, where the interference from different gases could greatly degrade the sensor's accuracy and reliability. Another challenge is that the sensing layer could be contaminated by real industrial environment where the oil mists, particle deposits, and polymerization may exist.

For measuring effective gas molecular weight and the specific heat ratio (k=Cp/Cv) variation, such as from gas charge compressor or compressor train for ethylene production process, it is not necessary to measure each component variation from a multi-component gas mixture. By considering the critical nature in measuring these gas characteristics for efficiency control and optimization, it will be helpful to have an online gas sensor for real-time operation for gas molecular weight and specific heat ratio measurements. Such a gas sensor should be insensitive to multi-component gas interference, oil mists, water vapor, tar deposit, and heavy hydrocarbon polymerization etc.

Accordingly, it is desirable to provide a low-cost gas sensing device and sensing instrumentation for the evaluation of gas characteristics to provide online accurate data for broad industrial gas applications such as measuring gas purity, gas quality, and gas cleanness. More specifically, there is a need to develop a new kind of gas sensor for determining gas characteristics, and in particular for measurement of gas molecular characteristics as online system for chemical petrochemical, refinery, and power generation industrial process control and optimization.

BRIEF DESCRIPTION

In one aspect, provided is a fiber gas sensor comprising a core fiber, a fiber cladding and a sensing matrix structure. The core fiber comprising at least one fiber Bragg grating defining at least one fiber Bragg grating region, an outer surface and a length. The fiber cladding is in contact with the core fiber along the entire length of the core fiber, the fiber cladding having an outer surface and a length. The sensing matrix structure is disposed upon the outer surface of the fiber cladding along a portion of the entire length of the fiber cladding and surrounding the fiber Bragg grating region. The sensing matrix structure comprising a high-coefficient of thermal expansion material based nano-structured trampoline matrix layer.

In another aspect, provided is a fiber gas sensor comprising a core fiber comprising at least one Bragg grating defining at least one fiber Bragg grating region, an outer surface and a length, a fiber cladding in contact with the core fiber along the entire length of the core fiber, the fiber cladding having an outer surface and a length and a sensing matrix structure disposed upon the outer surface of the fiber cladding along a portion of the entire length of the fiber cladding and surrounding the fiber Bragg grating region. The sensing matrix structure comprising a bonding layer, a high-coefficient of thermal expansion material based nano-structured trampoline matrix layer, and a capping layer. The bonding layer is disposed on the outer surface of the fiber cladding and having an outer surface and a length. The high-coefficient of thermal expansion material based nano-structured trampoline matrix layer is disposed on the outer surface of the bonding layer and having an outer surface and a length. The capping layer is disposed on the outer surface of the high-coefficient of thermal expansion material based nano-structured trampoline matrix layer and having an outer surface and a length.

In yet another aspect, provided is a component for a gas sensor comprising a core fiber comprising at least one fiber Bragg grating defining at least one fiber Bragg grating region, an outer surface and a length, a fiber cladding in contact with the core fiber along the entire length of the core fiber, the fiber cladding having an outer surface and a length and a sensing matrix structure disposed upon the outer surface of the fiber cladding along a portion of the entire length of the fiber cladding and surrounding the at least one fiber Bragg grating region. The sensing matrix structure comprising a bonding layer disposed on the outer surface of the fiber cladding and having an outer surface and a length, a high-coefficient of thermal expansion material based nano-structured trampoline matrix layer disposed on the outer surface of the bonding layer and comprising at least one of palladium (Pd), zinc (Zn), aluminum (Al), cobalt (Co), gold (Au) and copper (Cu) and having an outer surface and a length and a capping layer disposed on the outer surface of the high-coefficient of thermal expansion material based nano-structured trampoline matrix layer and having an outer surface and a length.

BRIEF DESCRIPTION OF THE DRAWING FIGURES

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
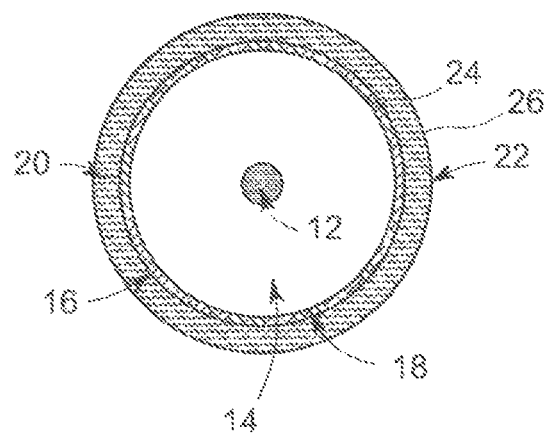
FIG. 1 is a cross-section of fiber gas sensor in accordance with an embodiment.

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

It is also understood that terms such as "top," "bottom," "outward," "inward," and the like are words of convenience and are not to be construed as limiting terms. Furthermore, whenever a particular feature of the invention is said to comprise or consist of at least one of a number of elements of a group and combinations thereof, it is understood that the feature may comprise or consist of any of the elements of the group, either individually or in combination with any of the other elements of that group.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified.

As discussed in detail below, embodiments include a fiber gas sensor comprising: a core fiber comprising at least one Bragg grating region, an outer surface and a length; a fiber cladding in contact with the core fiber along the entire length of the core fiber, the fiber cladding having an outer surface and a length; and a sensing matrix structure disposed on the outer surface of the fiber cladding along a portion of the entire length of the fiber cladding and surrounding the at least one Bragg grating region, the sensing matrix structure comprising: a bonding layer in contact with the fiber cladding layer, the bonding layering being disposed on the outer surface of the fiber cladding layer; a high-coefficient of thermal expansion (CTE) material based matrix layer in contact with the bonding layer, the high CTE material based matrix layer being disposed on the outer surface of the bonding layer; and a capping layer in contact with the high CTE material based matrix layer, the capping layer disposed on an outer surface of the high CTE material based matrix layer.

As used herein the term "Bragg grating region" is defined as a portion of the core fiber having a length $L_1$ and containing a Bragg grating such that the Bragg grating is centered at a distance about $L_1/2$ from the ends of the portion of the core fiber defining the Bragg grating region. The ends of the portion of the core fiber defining the Bragg grating region are, in general, indistinguishable from the core fiber and their locations are defined by the position and length of the Bragg grating contained within the Bragg grating region. As used herein the term "Bragg grating" is defined as a permanent periodic or/and quasi-periodic refractive index modulation in the core of an optical fiber over a length of typically 1-20 mm. In one embodiment, the Bragg grating may be created in the optic fiber by transversely illuminating the fiber with a periodic interference pattern generated by ultra-violet (UV) laser light. Those of ordinary skill in the art will appreciate that the core fiber used as the starting material for the creation of a core fiber containing a Bragg grating, will contain one or more photochemically reactive components which when exposed to relatively high energy laser light configured as, for example, an interference pattern, will react and thereby create the Bragg grating structure within the core fiber. The Bragg grating structure is highly stable in the sense that the relatively low energy light to which the Bragg grating is exposed during operation a fiber optic sensor containing the Bragg grating, is insufficient to cause rapid degradation of the Bragg grating created by exposure to the high energy laser light, or further reaction of unreacted photochemically reactive components within the core fiber used as the starting material. As used herein, the term "photochemically reactive component" includes materials which undergo either or both of photochemically allowed transformation and thermally allowed transformation in response to exposure to UV laser light. Typically, the length of Bragg grating region is from about 1.5 to about 100 times the length of the Bragg grating contained within the Bragg grating region, and the Bragg grating is more or less symmetrically disposed within the Bragg grating region. In one embodiment, the length of the Bragg grating region is from about 2 to about 50 times the length of the Bragg grating contained within the Bragg grating region. In another embodiment, the length of the Bragg grating region is from about 5 to about 10 times the length of the Bragg grating contained within the Bragg grating region.

As noted, the core fiber comprises an outer surface and a length and the core fiber includes at least one Bragg grating region. In one embodiment, the core fiber includes a plurality of Bragg grating regions. In one embodiment, the fiber Bragg grating is a thermally stable, tetrahedral fiber Bragg grating. In one embodiment, the fiber Bragg grating is an apodized fiber Bragg grating. In another embodiment, the fiber Bragg grating is a uniform fiber Bragg grating. In yet another embodiment, the fiber Bragg grating is a blazed and apodized fiber Bragg grating.

Core fibers for fiber optic sensors are known to those of ordinary skill in the art. Typically, the core fiber includes at least one material selected from the group consisting of silica, silicate glass, germanium doped silica, fluorided optical fiber material doped with fluorine, chlorine co-doped silicon dioxide, and the like. In one embodiment the core fiber includes a fluorine and germanium dioxide co-doped optical fiber material. In one embodiment, the core fiber includes at least one germanium oxide doped photosensitive material. In one embodiment, the core fiber is silica. In another embodiment, the core fiber includes a chlorine and germanium dioxide co-doped silicate glass. Non-limiting examples of doped silicate glass include germanium doped silica, nitrogen doped silicate, germanium dioxide doped silica, and the like.

In one embodiment, the core fiber has a diameter in a range from about 3 microns to about 15 microns. In another embodiment, the core fiber has a diameter in a range from about 6 microns to about 10 microns.

In one embodiment, the core fiber is polarization independent medium. In another embodiment, the core fiber is a polarization-maintaining medium. In yet another embodiment, the core fiber has a low transmission loss window at around 800 nm. In another embodiment, the core fiber has a low transmission loss window at around 1.55 microns. In one embodiment, the core fiber has a circular cross-section.

The core fiber is in contact with a fiber cladding along the entire length of the core fiber. The fiber cladding includes an outer surface and a length. In one embodiment, the refractive index of the fiber cladding is lower than the refractive index of the core fiber, so that light transmitted axially along the core fiber is substantially retained within the core fiber. In another embodiment, the fiber cladding includes at least one fluorine doped material. Examples of the fluorine doped cladding include but are not limited to silicon dioxide, silicon dioxide co-doped with germanium dioxide and fluorine, silicon dioxide co-doped with germanium dioxide, chlorine and fluorine, fluorine and phosphorus co-doped silicon dioxide.

In one embodiment, the fiber cladding includes a silicon dioxide co-doped with germanium dioxide and fluorine. In one embodiment, the fiber cladding includes a silicon dioxide co-doped from about 10 weight percent to about 20 weight percent germanium dioxide and from about 1.0 weight percent to about 2.5 weight percent fluorine. In another embodiment, the fiber cladding includes a silicon dioxide co-doped with about 8 weight percent germanium dioxide and 0.5 weight percent fluorine. In yet another embodiment, the fiber cladding is a fluorine and phosphorus co-doped silicon dioxide. In one embodiment, the fiber cladding includes silicon dioxide co-doped with from about 1 weight percent to about 1.5 weight percent phosphorus and from about 0.5 weight percent to about 2.5 weight percent fluorine.

In one embodiment, the fiber gas sensor provided includes a sensing matrix structure disposed upon the outer surface of the fiber cladding along a portion of the length of the fiber cladding and surrounding the fiber Bragg grating region. The sensing matrix structure includes a bonding layer, a high CTE material based nano-structured trampoline matrix layer, and a capping layer. As used herewith the term "matrix layer" and "nano-porous matrix layer" are also sometimes used to define the high CTE material based nano-structured trampoline matrix layer. The layers that comprise the sensing matrix structure may deposited and characterized using techniques known to one skilled in the art such as magnetron sputtering, and various chemical vapor deposition techniques. In one embodiment, the properties of the sensing matrix structure are dependent on the process of deposition of the sensing matrix structure, and more particularly the bonding layer, upon the fiber cladding. Several known techniques may be employed to dispose the bonding layer upon the fiber cladding, the nano-structured trampoline matrix layer upon the bonding layer and the capping layer upon the nano-structured trampoline matrix layer, examples include but are not limited to sandwiched and multilayered structures, and the like. In one embodiment, applying the sensing matrix structure upon the fiber cladding includes a post annealing step at a temperature in the range from about 150° C. to about 300° C. to eliminate or reduce internal residual stresses in the sensing matrix structure, in addition to turning part of the amorphous layer into a nano-structured porous matrix. In one embodiment, the high CTE material based nano-structured trampoline matrix layer has an overall thickness of approximately 1.0-20.0 microns. The bonding layer has an overall thickness of approximately 0.03-0.10 microns and the capping layer has an overall thickness of approximately 0.05-0.2 microns.

Referring to FIG. 1, the figure shows a cross-section of the fiber gas sensor 10 in accordance with one embodiment of the invention. The fiber gas sensor 10 includes a core fiber 12 and a fiber cladding 14 in contact with the core fiber 12. The core fiber 12 includes at least one Bragg grating region (not shown). A sensing matrix structure 15 is disposed on an outer surface 18 of the fiber cladding. The sensing matrix structure 15 is comprised of a bonding layer 16, a high CTE material based nano-structured trampoline matrix layer 20, and a capping layer 22. The bonding layer 16 is disposed on the outer surface 18 of the fiber cladding 14. The high CTE material based nano-structured trampoline matrix layer 20 is disposed on an outer surface 24 of the bonding layer 16. The capping layer 22 is disposed on an outer surface 26 of the high CTE material based nano-structured trampoline matrix layer 20, and encasing the various layers defining the sensing portion of the fiber. Although not shown in FIG. 1, the core fiber 12 and the fiber cladding 14 may include more than one layer of silica.

Figure 2:
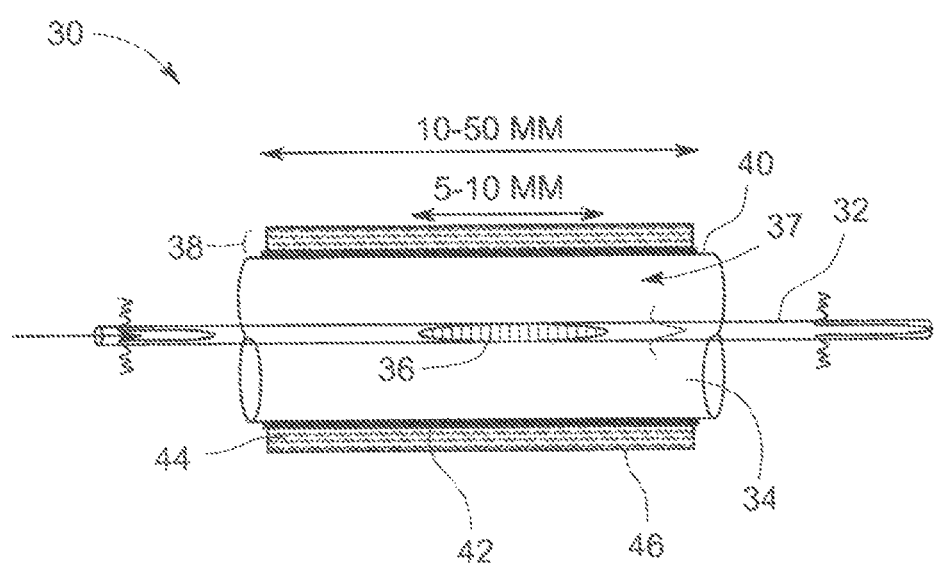
FIG. 2 is a fiber gas sensor in accordance with an embodiment.
Figure 3:
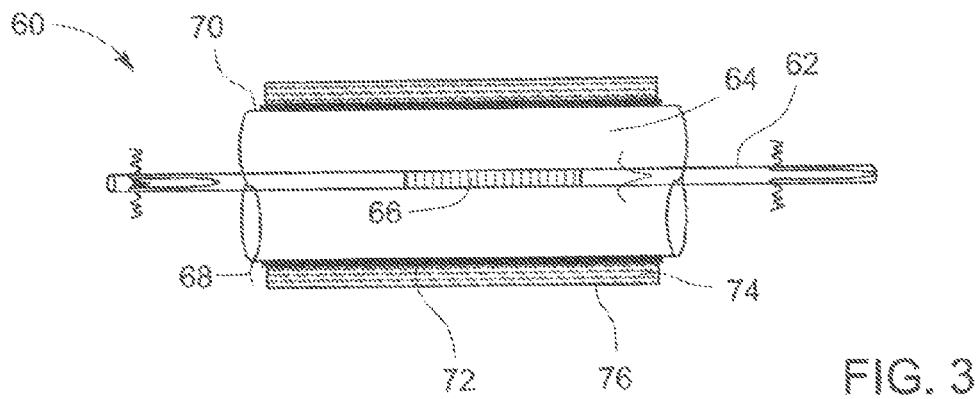
FIG. 3 is a fiber gas sensor in accordance with an embodiment.
Figure 4:
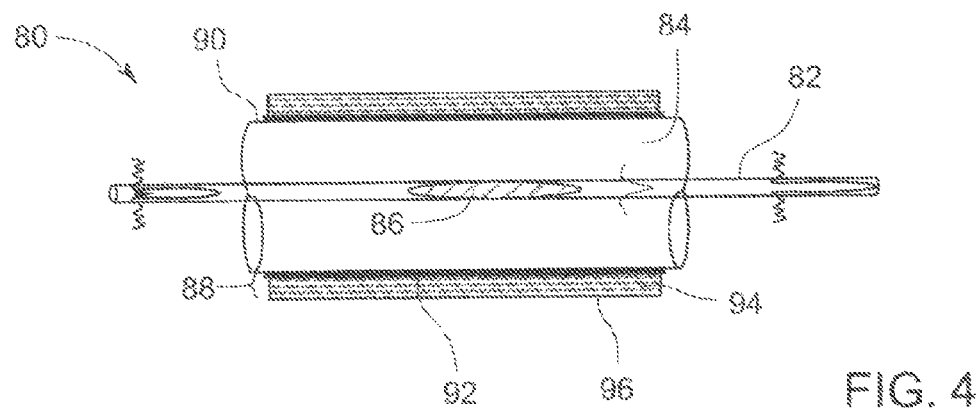
FIG. 4 is a fiber gas sensor in accordance with an embodiment.

FIGS. 2-4 are embodiments of a fiber gas sensor including a grating structure having uniform, apodized, and apodized/blazed refractive index modulation profiles. More specifically, illustrated in FIG. 2 is a fiber gas sensor 30 according to one embodiment of the invention. The fiber gas sensor 30 includes a core fiber 32 and a fiber cladding 34 in contact with the core fiber 32. The core fiber 32 includes at least one Bragg grating 36. In this particular embodiment, the Bragg grating 36 is configured as an apodized fiber Bragg grating having an overall length of between approximately 5-10 mm and defining a fiber Bragg grating region 37 having an overall length of between approximately 10-50 nm. A sensing matrix structure 38 is disposed on the outer surface 40 of the fiber cladding 34, and surrounding the fiber Bragg grating 36. In the illustrated embodiment, the sensing matrix structure 38 is configured having an overall length so as to surround the fiber Bragg grating region 37 thereby being approximately 10-50 mm. The sensing matrix structure 38 is comprised of a bonding layer 42, a high CTE material based nano-structured trampoline matrix layer 44 and a capping layer 46. The bonding layer 42 is disposed on the outer surface 40 of the fiber cladding 34. The high CTE material based nano-structured trampoline matrix layer 44 is disposed on an outer surface of the bonding layer 42. The capping layer 46 is disposed on an outer surface of the high CTE material based nano-structured trampoline matrix layer 44, and encasing the various layers defining the sensing portion of the fiber 30.

FIG. 3 depicts a fiber gas sensor 60 in accordance with another embodiment of the invention. The fiber gas sensor 60 includes a core fiber 62 and a fiber cladding 64 in contact with the core fiber 32. The core fiber 62 includes at least one Bragg gratings 66. In this particular embodiment, the Bragg grating 66 is configured as a uniform fiber Bragg grating. A sensing matrix structure 68 is disposed on the outer surface 70 of the fiber cladding 64, and surrounding the fiber Bragg grating 66. The sensing matrix structure 68 is comprised of a bonding layer 72, a high CTE material based nano-structured trampoline matrix layer 74 and a capping layer 76. The bonding layer 72 is disposed on the outer surface 70 of the fiber cladding 64. The high CTE material based nano-structured trampoline matrix layer 74 is disposed on an outer surface of the bonding layer 72. The capping layer 76 is disposed on an outer surface of the high CTE material based nano-structured trampoline matrix layer 74, and encasing the various layers defining the sensing portion of the fiber 60.

FIG. 4 depicts a fiber gas sensor 80 in accordance with another embodiment of the invention. The fiber gas sensor 80 includes a core fiber 82 and a fiber cladding 84 in contact with the core fiber 82. The core fiber 82 includes at least one Bragg gratings 86. In this particular embodiment, the Bragg grating 86 is configured as a blazed and apodized fiber Bragg grating. A sensing matrix structure 88 is disposed on the outer surface 90 of the fiber cladding 84 and surrounding the fiber Bragg grating 86. The sensing matrix structure 88 is comprised of a bonding layer 92, a high CTE material based nano-structured trampoline matrix layer 94 and a capping layer 96. The bonding layer 92 is disposed on the outer surface 90 of the fiber cladding 84. The high CTE material based nano-structured trampoline matrix layer 94 is disposed on an outer surface of the bonding layer 92. The capping layer 96 is disposed on an outer surface of the high CTE material based nano-structured trampoline matrix layer 94, and encasing the various layers defining the sensing portion of the fiber 80.

In the embodiments illustrated in FIGS. 2-4, each sensing device 30, 60, 80 is an integration of at least one of a plurality of fiber grating structures (uniform, apodized, and blazed/apodized) with the sensing matrix structure 38, 68, 88, comprised of the bonding layer, the high CTE material based nano-structured trampoline matrix layer and the capping layer, surrounding the fiber cladding and grating length. During operation, the guided waves are confined inside their respective fiber core, and a reflected signal from the grating, at Bragg resonant condition, will be detected by an optical signal readout system (not shown).

Figure 5:
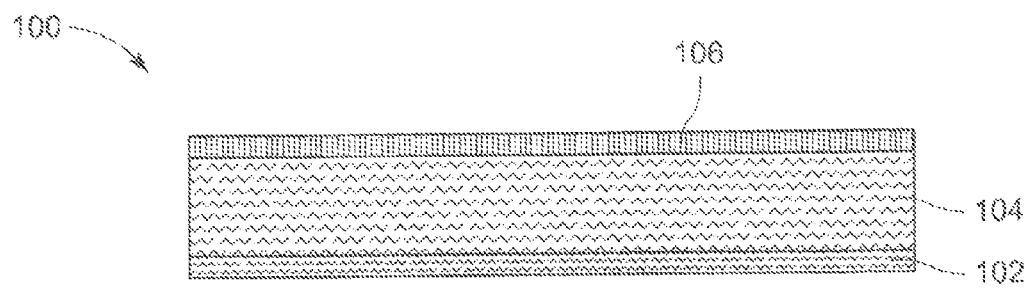
FIG. 5 is a section of a sensing matrix structure surrounding a fiber Bragg grating cladding surface in accordance with an embodiment.

FIG. 5 depicts a sensing matrix structure 100, generally similar to the sensing matrix structure 38, 68, 88 depicted in FIGS. 2-4, respectively. More specifically, illustrated is the sensing material nanostructure that surrounds the fiber cladding of the Bragg grating region length of a fiber gas sensor according to an embodiment. The disclosed sensing matrix structure 100 is comprised of a bonding layer 102, generally similar to the bonding layer 42, 72 and 92 depicted in FIGS. 2-4, respectively, a high coefficient of thermal expansion material based nano-structured trampoline matrix layer 104, generally similar to the nano-structured trampoline matrix layer 44, 74 and 94 depicted in FIGS. 2-4, respectively, and a capping layer 106, generally similar to the capping layer 46, 76 and 96 depicted in FIGS. 2-4, respectively. In the illustrated embodiment, the bonding layer 102 may be disposed on an outer surface of the fiber cladding layer, generally similar to the outer surface 40, 70, 90 of the fiber cladding layer 34, 64, 84 depicted in FIGS. 2-4. The bonding layer 102 is deposited using any well-known ambient substrate temperature deposition techniques, such as DC magnetron sputtering, electron-beam sputtering, chemical vapor deposition, or the like. The bonding layer 102 may be comprised of a titanium (Ti) based material, Ti- oxide based material, or the like, and configured having a total thickness of approximately 30-100 nm. The high coefficient of thermal expansion material based nano-structured trampoline matrix layer 104 may be disposed on an outer surface of the bonding layer 102. The high CTE material based nano-structured trampoline matrix layer 104 may be comprised of copper (Cu), cobalt (Co), nickel (Ni), zinc (Zn), gold (Au), or their alloys, and configured having a total thickness of approximately 5-20 μm. The capping layer 106 may be disposed on an outer surface of the high CTE material based nano-structured trampoline matrix layer 104. The capping layer 106 is deposited using any well-known ambient substrate temperature deposition techniques, such as sputtering, or the like. The capping layer 106 may be comprised of an anti-corrosion and oxidation based material, such as palladium (Pd), nickel (Ni), titanium (Ti), and gold (Au), or their alloys, and configured having a total thickness of approximately 50-200 nm. Subsequent to deposition of the layers 102, 104 and 106 about the fiber Bragg grating region that comprise the sensing matrix structure 100, the structure undergoes a post deposition annealing process in an oxidized environment. In one embodiment, the sensing matrix structure 100 may undergo a 150-300° C. annealing process for approximately 100 hours. Subsequent to thermal treatment, observed Atomic Force Microscopy (AFM) imaging has shown the sensing matrix structure 100 to include a vertical or pillar-like nano-structured texture for gas molecular interaction and/or spaghetti-like surface textures that reflect trampoline-like structures.

Figure 6:
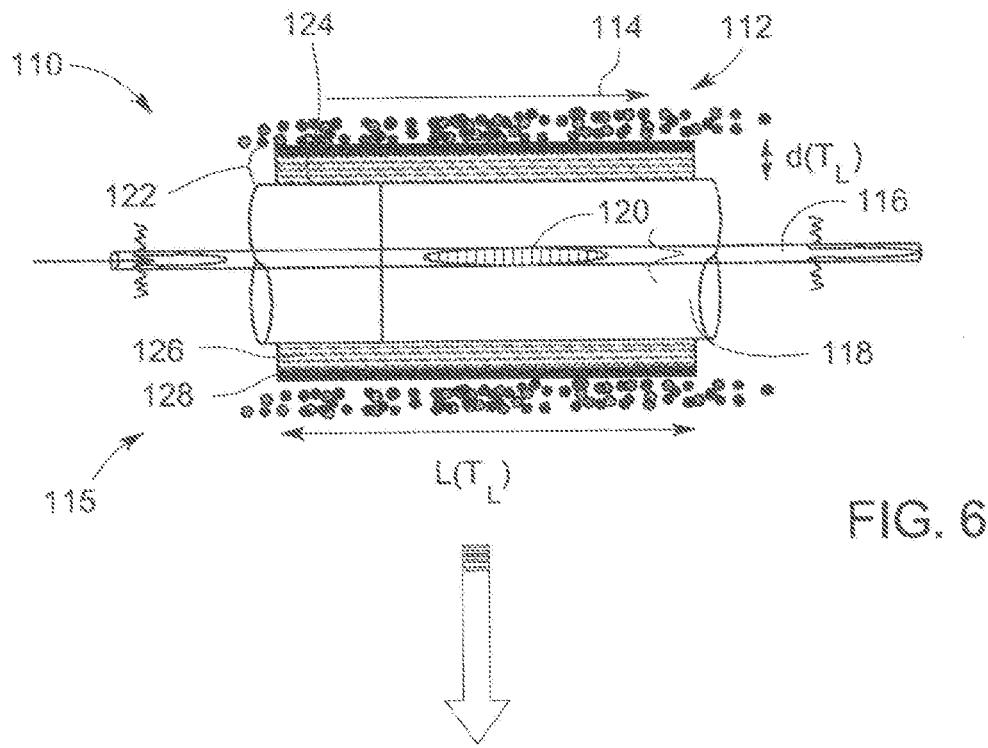
FIG. 6 illustrates gas molecular interaction with a fiber gas sensor in accordance with an embodiment.
Figure 7:
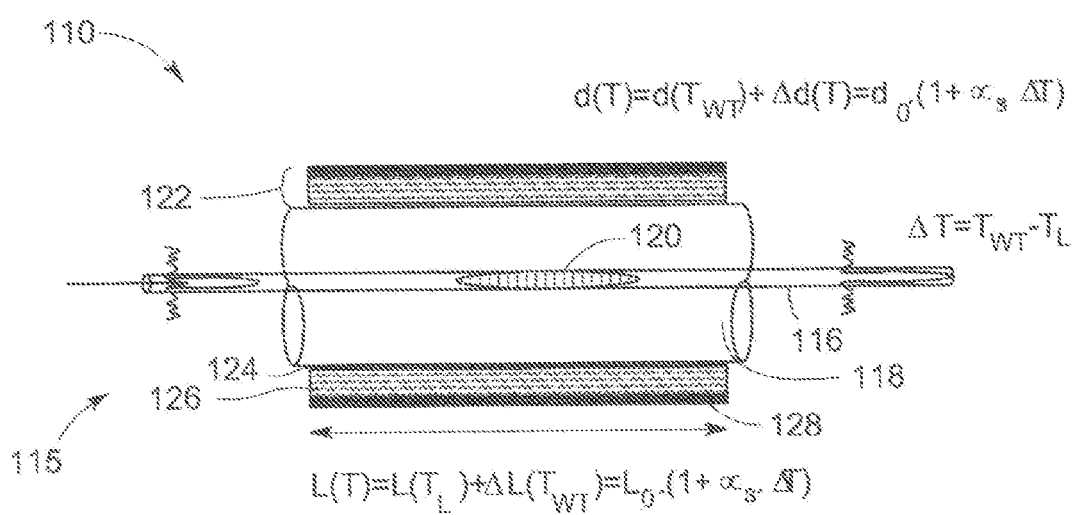
FIG. 7 illustrates the trampoline thermal expansion process while gas molecular is removed from a fiber gas in accordance with an embodiment.

FIGS. 6 and 7 illustrate the working principle of a nano-structured trampoline and fiber Bragg grating integrated fiber gas sensor 110, and more particularly a fiber sensor component 115, according to an embodiment including a nano-structured trampoline sensing matrix structure 122, similar to sensing matrix structure 100 of FIG. 5. The sensing matrix structure 122 is configured to include a nano-structured trampoline matrix layer 126 as a smart skin for gas molecular detection by a fiber Bragg grating 120 under external thermal modulation. Such a nanomaterial sensing matrix structure 122 and fiber Bragg grating integrated structure is based on thermal energy absorption of gas molecular from a high-thermal-energy loaded sensing device that is at high tensile strain status. Subsequent to thermal energy loss, due to gas molecular heat absorption, the reduced tensile strain from the nano-structured trampoline matrix layer 126 induces a compressed strain on the sensor's fiber cladding 118 so that the Bragg resonant wavelength downshift depends upon gas molecular species. FIGS. 6 and 7 illustrate how thermal modulation by molecular thermal energy absorption from an energized trampoline structure sensing matrix structure induces thermal strain for gas molecular detection. More specifically, illustrated is a portion of the fiber gas sensor 110, and more specifically the fiber sensor 115, according to an embodiment disposed in the presence of a gas flow 112 comprised of a plurality of gas molecules 113. In this particular embodiment, the gas flow 112 is flowing from left to right as indicated by arrow 114. The fiber gas sensor 115 is generally comprised of a core fiber 116, the fiber cladding 118 in contact with the core fiber 116 and the nano-structured trampoline sensing matrix structure 122. The core fiber 116 includes the at least one fiber Bragg grating 120, defining a fiber Bragg grating region 121. The trampoline structure sensing matrix structure 122 is disposed on the outer surface of the fiber cladding 118 and surrounding the fiber Bragg grating 120. The nano-structured trampoline sensing matrix structure 122 is generally comprised of a bonding layer 124, the high CTE material based nano-structured trampoline matrix layer 126, and a capping layer 128.

During operation under low-energy (LE) conditions, as best illustrated in FIG. 6, and subsequent to the gas molecules 113 absorbing the energy from trampoline structure sensing matrix structure 122, the sensing matrix structure 122 has a length $L(T_L)$, and thickness $d(T_L)$, where "L" corresponds to low-energy (LE) status of the trampoline structure. The fiber gas sensor 115 will show a relative resonant wavelength shift from its ambient temperature, $T_{A, by}$, $$\Delta \lambda_{LE} = \lambda_B \cdot \left[ \kappa_\varepsilon \cdot \left( \frac{Y_o}{1+y} \right) \cdot (\alpha_S - \alpha_f) \cdot (T_L - T_A) + \kappa_T \cdot (T_{WT} - T_A) \right],$$

and $y = \dfrac{Y_o r_1^2}{Y_1 \cdot (r_2^2 - r_1^2)}$

Where $\lambda_B$ is ambient fiber gas sensor corresponding Bragg resonant wavelength, $\kappa_\varepsilon$ is fiber sensor strain sensitivity (1.5-2.0 pm/με), α is coefficient of thermal expansion of sensing material (S) and fiber material (f), where $\alpha_S \gg \alpha_f$, $Y_0$ and $Y_1$ are Young's modulus of fiber and sensing material. The sensing layer thickness is $t = r_2 - r_1$, where $r_1$ and $r_2$ are radius of bare fiber and sensing layer coated fiber. In this case, the fiber gas sensor sensitivity is determined by thermal expansion effect and Young modulus of the selected sensing material.

When the gas molecular is fully discharged, the trampoline structure in the sensing matrix structure 122 is recovered back to high-energy (HE) status as best illustrated in FIG. 7 or to working temperature value. The corresponding fiber sensor resonant wavelength is shifted to:

$$\Delta \lambda_{HE} = \lambda_B \cdot \left[ \kappa_\varepsilon \cdot \left( \frac{Y_o}{1+y} \right) \cdot (\alpha_S - \alpha_f) \cdot (T_{WT} - T_A) + \kappa_T \cdot (T_{WT} - T_A) \right],$$

The absolute response amplitude from each gas molecular jumping process can be written as:

$$\Delta \lambda = \Delta \lambda_{HE} - \Delta \lambda_{LE} = \lambda_B \cdot \left[ \kappa_\varepsilon \cdot \left( \frac{Y_o}{1+y} \right) \cdot (\alpha_S - \alpha_f) \cdot (T_{WT} - T_L) \right]$$

because the gas molecular thermal energy absorption is depending upon thermal energy loss by convective gas molecular interaction process. For molar molecular energy absorption under a flow rate of "f" and gas flow cross-section of "A", the thermal energy loss rate is $q = \Delta Q/\Delta t = h \cdot A \cdot (T_{WT} - T_L)$ where h is heat convection coefficient of the fiber sensor.

At a given gas flow 114 condition, the thermal energy loss can be described by, $\Delta Q = C_p \cdot \Delta m = f \cdot \Delta t \cdot C_p \cdot \overline{\omega}/N_A$ where NA is Avogadro's number ($6.022 \times 10^{23}$ mol$^{-1}$), $C_p$ is specific heat coefficient of the gas, $\overline{\omega}$ is molecular weight.

Thus, the thermal strain modulation between low-energy (LE) and high-energy (HE) statuses leads to the fiber sensor's response amplitude being indicative of an effective molecular weight, $$\Delta \lambda(\overline{\omega}) = \lambda_B \cdot \kappa_\varepsilon \cdot \left( \frac{Y_o}{1+y} \right) \cdot (\alpha_S - \alpha_f) \cdot f \cdot c_p \cdot \overline{\omega}/(h \cdot A \cdot N_A) = \xi \cdot \overline{\omega}$$

For real-time gas quality or purity analysis, the molecular weight variation can be expressed as:

$\overline{\omega}(t) = \overline{\omega}(0) + \Delta\overline{\omega}(t)$, where $\Delta\overline{\omega}/\overline{\omega} \ll 1$ Furthermore, the gas molecular weight can be expressed as:

$\Delta\overline{\omega}(t) = \overline{\omega}(0) \cdot [1 + \Delta\lambda(\overline{\omega}(t))/\Delta\lambda(\overline{\omega}(0))]$ where $\Delta\lambda(\overline{\omega}(0)) = \xi \cdot \overline{\omega}(0)$.

Figure 8:
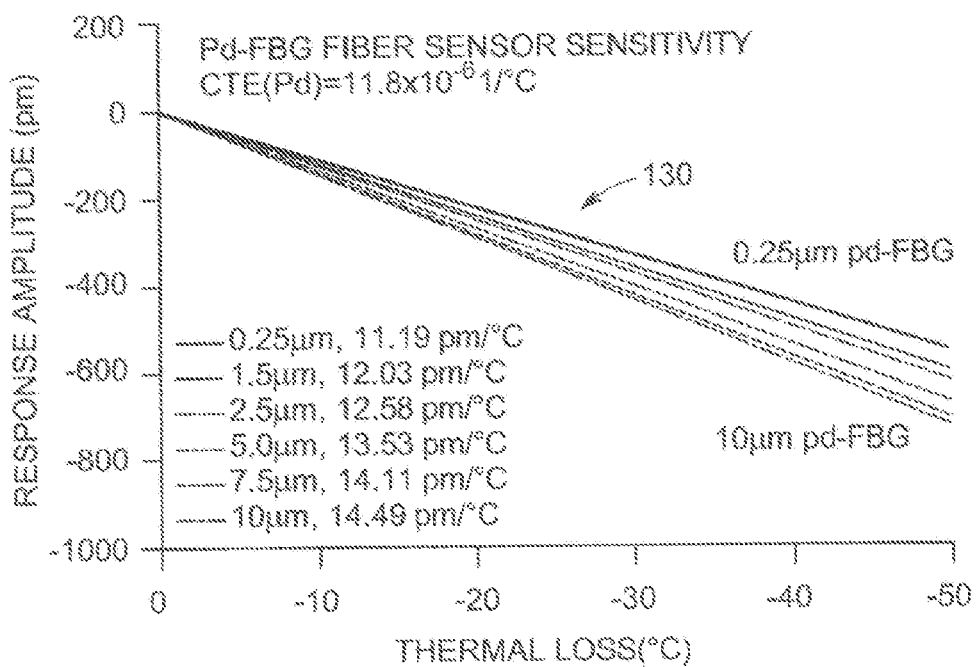
FIG. 8 illustrates simulated palladium (Pd) based trampoline matrix thickness, thermal strain sensitivity and thermal response characteristics versus the gas molecular induced thermal loss according to an embodiment.
Figure 9:
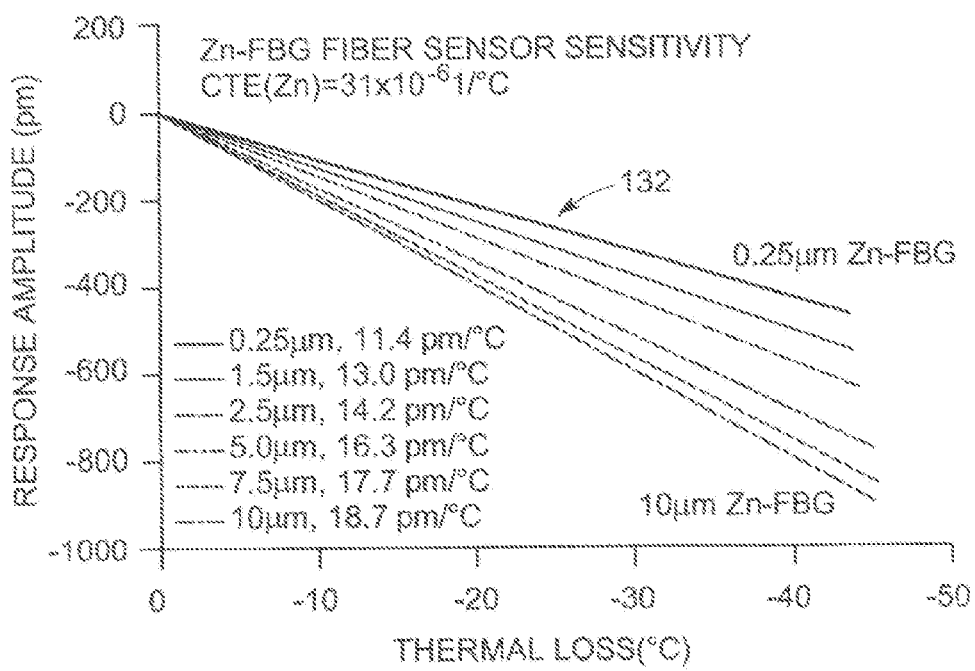
FIG. 9 illustrates simulated zinc (Zn) based trampoline matrix thickness, thermal strain sensitivity and thermal response characteristics versus the gas molecular induced thermal loss according to an embodiment.

FIGS. 8 and 9 provide data demonstrating the inclusion of differing metal materials with differing thermal expansion capabilities for the nano-structured trampoline matrix layer 126 of FIGS. 6 and 7. As indicated, the thermal strain and sensitivity may be artificially enhanced for small and light molecular detection. The plots 130 of FIGS. 8 and 9 illustrate the thermal strain induced sensitivity dependence upon the thermal energy loss by gas molecular "jumping" on the sensing matrix structure surface. When the nano-structured trampoline sensing matrix structures used for plots 130 and 132 were comprised of a palladium (Pd) and zinc (Zn) based materials having an overall thickness of from 0.25 to 10 microns according to an embodiment and was deposited by one or more techniques known those of ordinary skill in the art. The data clearly shows in each figure the thermal response characteristics, and more particular response amplitudes, versus the gas molecular induced thermal loss ($T_{WT}$-$T_L$). As indicated by plots 130 and 132, a thicker nano-structured trampoline matrix layer 126 may introduce higher thermal strain on the fiber gas sensor 115. In addition, a heavy gas molecular may introduce a high thermal absorption and relative large wavelength downshift. Accordingly, a higher thermal modulation induced thermal strain enables higher molecular detection sensitivity.

Figure 10:
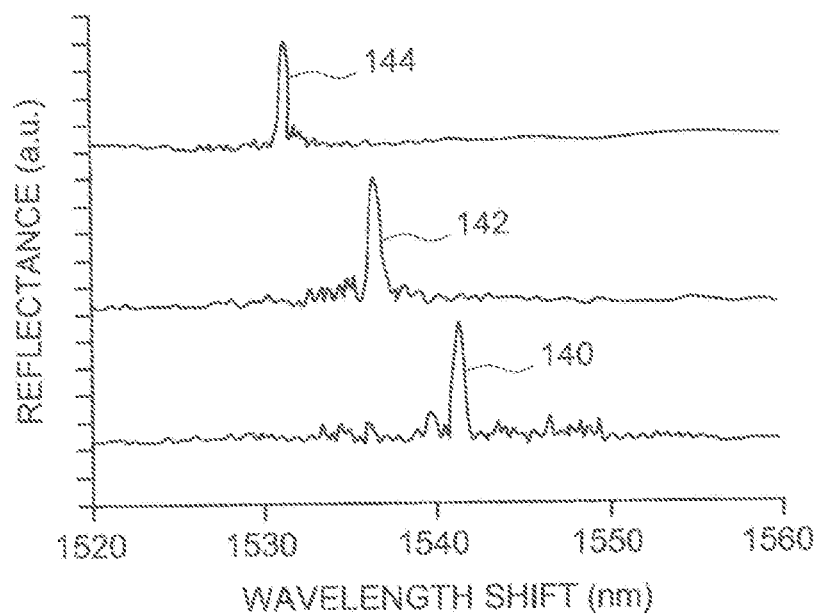
FIG. 10 illustrates the fiber gas sensor spectra in terms of wavelength shift for a first fiber gas sensor, a second fiber gas sensor and a third fiber gas sensor according to an embodiment.

FIG. 10 provides data from three fiber gas sensors generally configured as described according to FIGS. 6 and 7, and more particularly provides data of the wavelength shift as evidenced in a plot 140 of a first fiber gas sensor, a plot 142 of a second fiber gas sensor and a plot 144 of a third fiber gas sensor. The shift in wavelengths of plots 140, 142, and 144 demonstrates the fiber gas sensor (FGS) spectra from a prototype with the first fiber gas sensor and the second fiber gas sensor being for differential signal process, and for the third fiber gas sensor being for gas inlet temperature monitoring. The three FGS sensors have their Bragg resonant wavelengths in-between 1530 nm to 1550 nm and about 0.3 nm line width at 3 dB. The nano-structured trampoline layer in each sensor has a nominal thickness of 5 micron made from copper (Cu) and fabricated with a magnetron process under DC 200W power.

Figure 11:
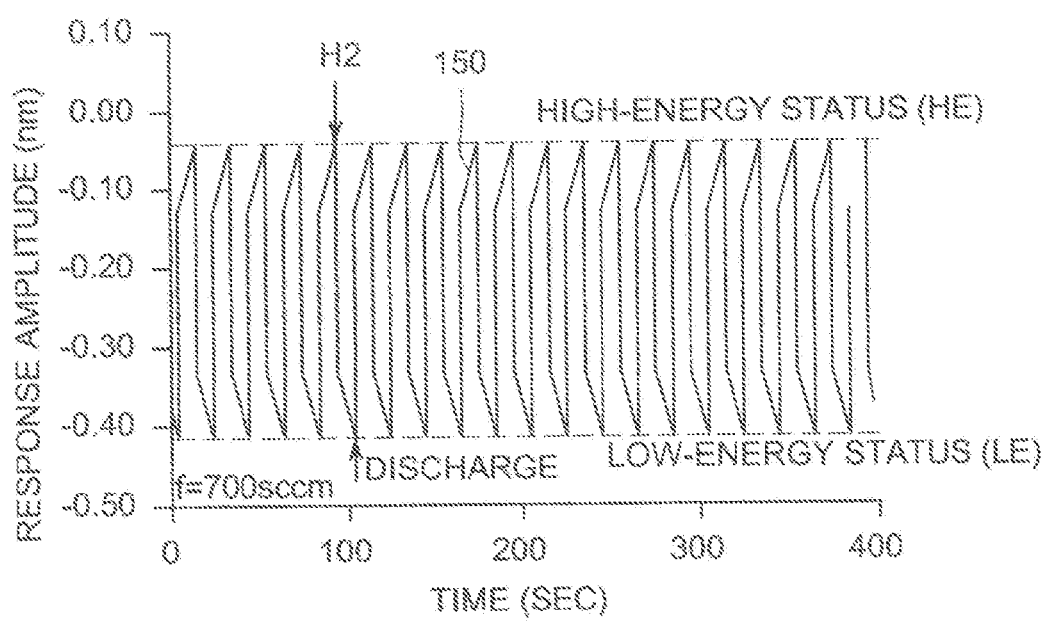
FIG. 11 illustrates the thermally modulated signal for a trampoline structure response to hydrogen ($H_2$) gas molecules at low-energy (LE) status and high-energy (HE) status according to an embodiment.
Figure 12:
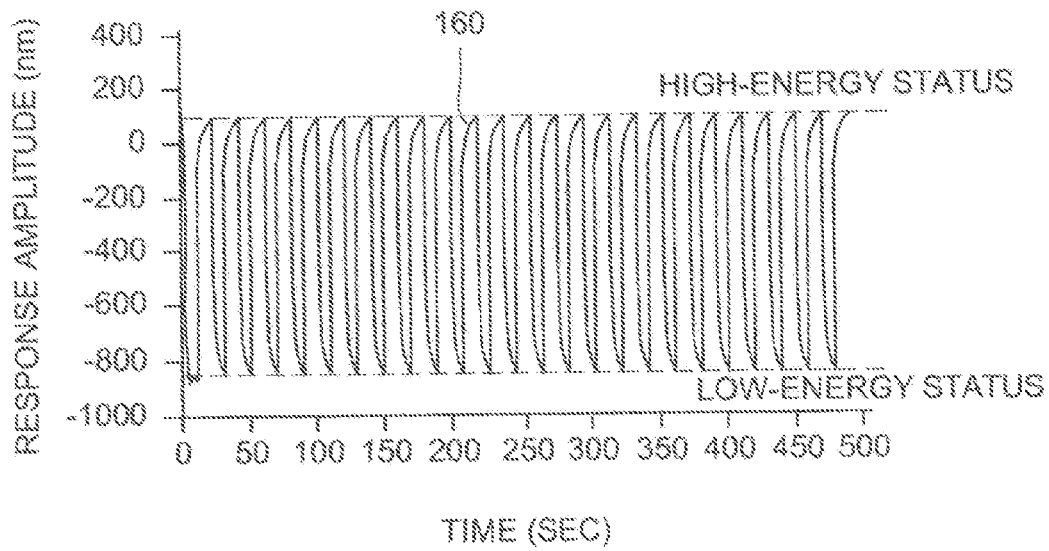
FIG. 12 illustrates the thermally modulated signal for a trampoline structure response to hydrocarbon gas molecules at low-energy (LE) status and high-energy (HE) status according to an embodiment.
Figure 13:
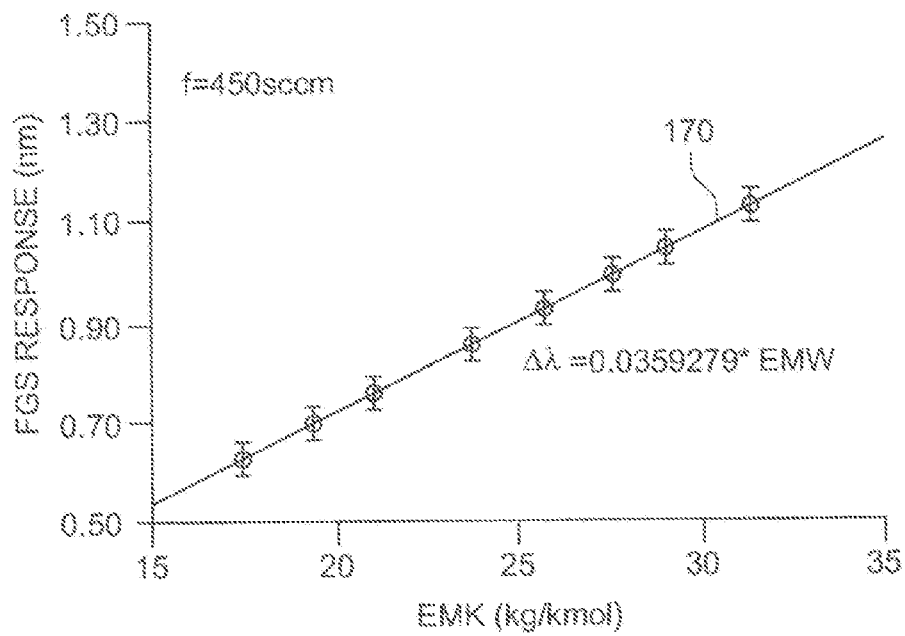
FIG. 13 illustrates a measured fiber gas sensor (FGS) response amplitude versus the gas effective molecular weight (EMW) according to an embodiment.
Figure 14:
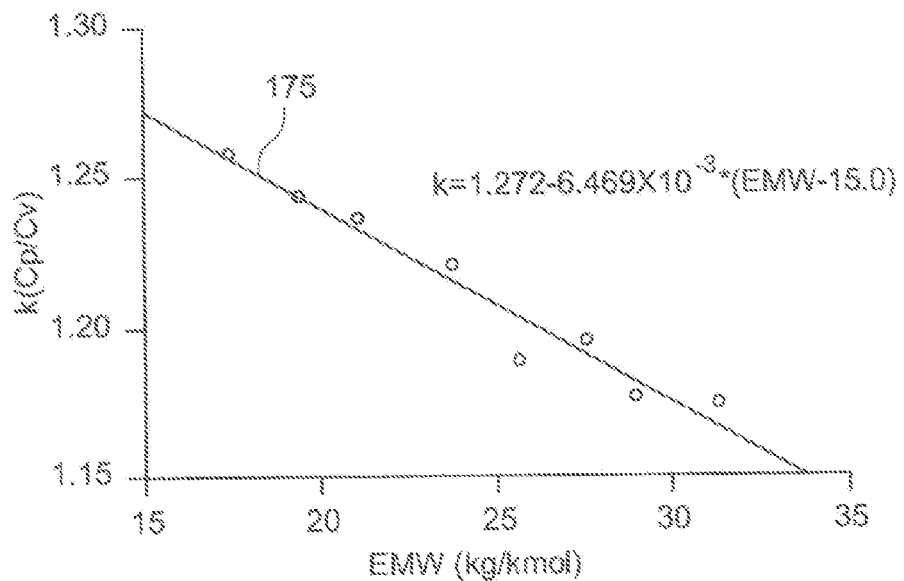
FIG. 14 illustrates molecular weight and gas density transfer functions obtained for gas molecular weight greater from 2 kg/kmol to 17 kg/kmol according to an embodiment.

FIG. 11 provides data demonstrating an experimental measured response amplitude from hydrogen ($H_2$) gas analysis under 700 sccm (standard cubic centimeter per minute) flow rate, depicted as plot 150. The fiber gas sensor response follows alternative gas in and discharge. The obtained response amplitude between the high-energy status (HE) and low-energy status (LE) is about 0.34 nm. FIG. 12 provides data demonstrating experimental measured response amplitude from a hydrocarbon gas mixture (22.94% H2, 23.01% CH4, 24.26% C2H6, etc.) under 450 sccm (standard cubic centimeter per minute) flow rate, depicted as plot 160. In the experimental examples, the thermal modulation is controlled by an external solid state relay with cycle duration of 5-20 sec for each gas molecular interaction with the fiber gas sensor. The differential response amplitude between a low-energy status and a high-energy status is, then, calibrated with standard molecular weight analysis. FIG. 13 demonstrates data showing the measured response amplitude versus effective molecular weight (EMW or $\bar{\omega}$) as plot 170, which is substantially a linear function in the range of from 17 kg/kmol to 32 kg/kmol. From obtained effective molecular weight (EMW or $\bar{\omega}$), the ratio of the specific heat (k=Cp/Cv) can be calculated by k=k(0)+b*EMW. FIG. 14 has shown the experiment determined k dependence upon the EMW or $\bar{\omega}$, as plot 175.

Figure 15:
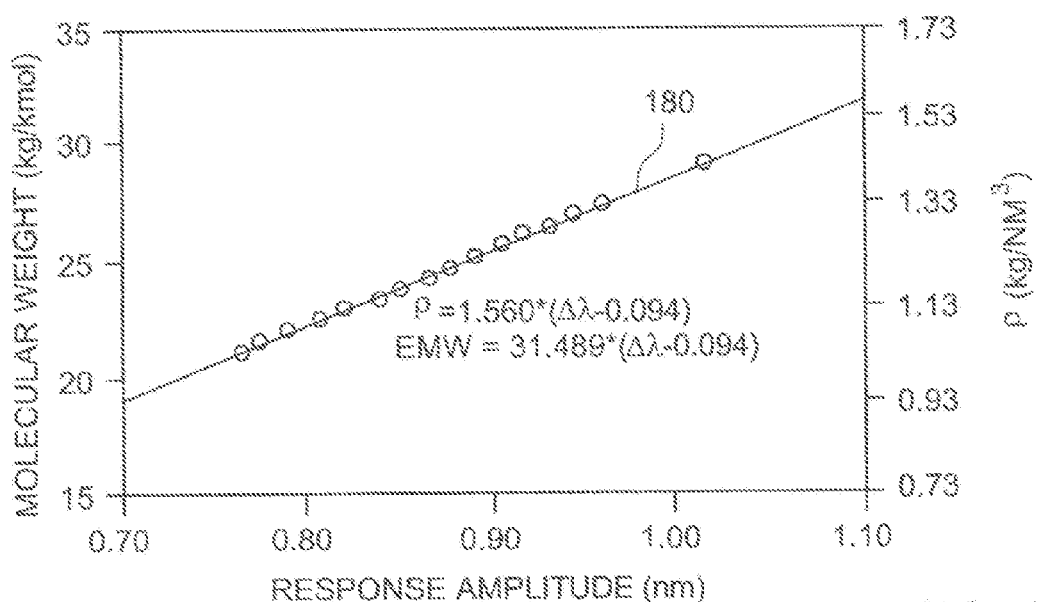
FIG. 15 illustrates molecular weight and gas density transfer functions obtained for gas molecular weight greater from 22 kg/kmol to 28 kg/kmol range according to an embodiment.
Figure 16:
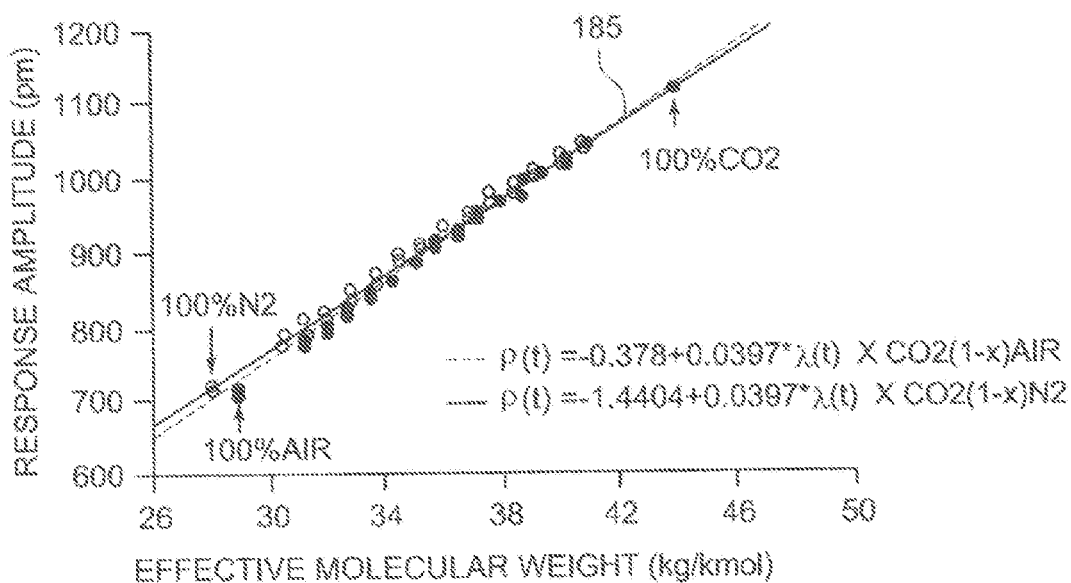
FIG. 16 illustrates molecular weight and gas density transfer functions obtained for gas molecular weight greater from 28 kg/kmol to 44 kg/kmol range according to an embodiment.
Figure 17:
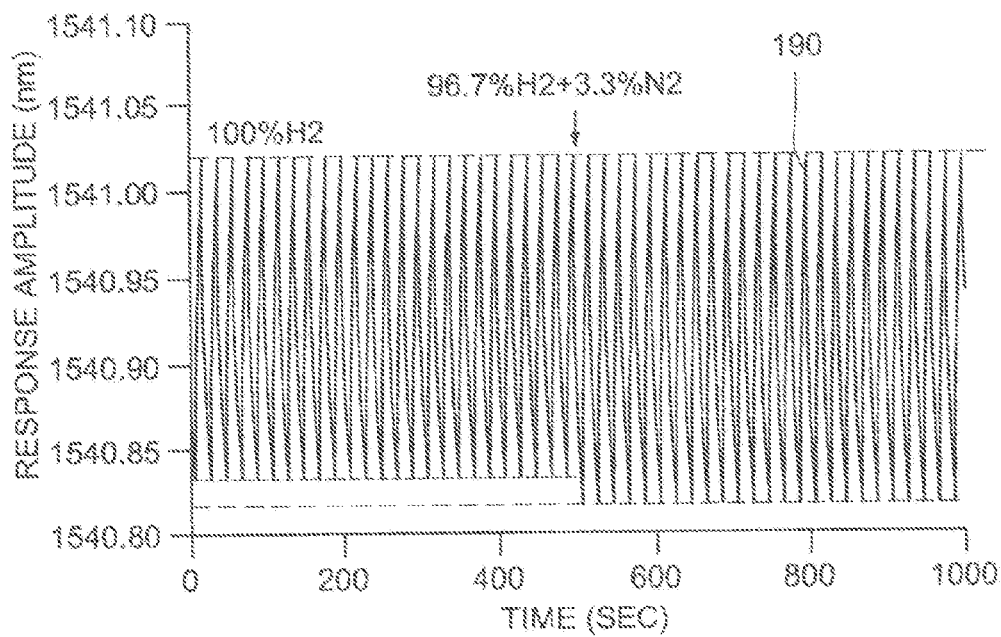
FIG. 17 illustrates molecular weight and gas density transfer functions obtained for gas molecular weight greater from 2 kg/kmol to 2.86 kg/kmol range according to an embodiment.

FIGS. 15-17 illustrate the broad capability of a fiber gas sensor as described herein for a wide range of molecular weight detection. More particularly, FIGS. 15-17 illustrate gas molecular analyzation from 2 to 44 kg/kmol range from lab feasibility studies. Each range of the molecular weight could be used for different applications. Referring more specifically to FIG. 15, demonstrated is data showing molecular weight and gas density transfer functions, as plot 180, obtained for gas molecular weight greater from 22 kg/kmol to 28 kg/kmol range according to an embodiment. This gas molecular weight is typically for ethylene production hydrocarbon gas feedstock. The molecular weight change from 22 kg/kmol to 28 kg/kmol may be an indication of the compressor fouling formation and a reduction or loss of the polytropic efficiency. FIG. 16 illustrates corresponding specific heat ratio, k, as a function of effective molecular weight according to an embodiment. More specifically, FIG. 16 demonstrates data showing the measured gas molecular weight, as plot 185, from 28 kg/kmol to 44 kg/kmol, which is typical for heavy sour gas analysis ($CO_2$, $H_2S$) for oil/gas extraction, refinery, and petrochemical process. FIG. 17 demonstrates data showing the measured hydrogen gas molecular weight, as plot 190, from 2 kg/kmol to 2.86 kg/kmol, which is typical for MW $H_2$-cooled generator hydrogen purity gas analysis. This may give an indication of the fiber gas sensor's sensitivity to 3.3% $N_2$ contamination from $H_2$ gas when 95%-98% $H_2$ purity is required for generator efficiency control.

In one embodiment, a fiber optic gas sensor, and more particularly a fiber optic sensor component, is disclosed including a core fiber, containing a Bragg grating and a fiber cladding disposed about. Disposed about an outer surface of the fiber cladding is a band of high CTE metal (such as Au, Pd, Zn, Co, Al, Cu, or similar high CTE metal, or their alloy) that is tightly bound to the fiber cladding which has a much lower CTE. Meanwhile, these high CTE materials are also high thermal conductive materials. When the fiber optic gas sensor is heated the mismatch in CTE either expands or compresses the Bragg grating, and changes its Bragg resonant characteristics as evidenced by a change in Bragg wavelength. If a fiber gas sensor is heated, and then exposed to a flowing gas stream, information regarding the composition of the gas can be realized by monitoring the Bragg grating wavelength downshift as the gas molecular absorbs the heat from the high CTE matrix layer. If the gas molecular is metered as a sample stream from a flowing gas stream, and in such a way that a constant number of molecules (T, P, V) are present, one can determine (using standards) the composition of the gas stream. In addition, changing gas compositions under constant T, P, V measurement conditions may be realized. During each cycle of gas molecules interact with sensing matrix structure and discharge, the sensing matrix structure has experienced contraction and expansion, where the expansion is controlled by the working temperature, while the contraction only depends upon the gas composition or molecular mass. Such a thermally modulation induced sensing matrix structure volume variation is similar to a molecular trampoline, and the trampoline amplitude is determined by the molecular weight.

Disclosed is a gas molecular detection device with a nano-structured trampoline layer as smart skin for gas molecular detection by a fiber Bragg grating under external thermal modulation. Such a nanomaterial and fiber grating integrated structure is based on thermal energy absorption of gas molecular from high-thermal-energy loaded sensing device that is at high tensile strain status. Subsequent to thermal energy loss due to gas molecular heat absorption, the reduced tensile strain from trampoline matrix induces a compressed strain on the sensor's fiber cladding so that the Bragg resonant wavelength shift depends upon gas molecular species. The sensing device is able to identify single-component gas, binary-component gas mixture, and multi-gas mixture by analyzing effective molecular (molar) weight variation. The nano-structured trampoline matrix material is configured having a porous structure in plan, and a layer-by-layer sputtering process leads to a multilayered trampoline-like matrix. When the porosity is far less than its percolation threshold such a structure can be formed as a trampoline-like matrix by a thermal post-treatment process.

The provided gas molecular mass detection technology can be used to online measure gas molecular and its effective molecular molar weight for single-component, binary-component, and multi-component gas mixture analysis. The thermal modulated nano-structured trampoline gas sensor for gas molecular detection is operable regardless of its purity, cleanness, and uncertain gas temperature. The higher thermal expansion coefficient of the nano-structure trampoline matrix material produces a measurable thermal strain for shifting the fiber Bragg grating resonant wavelength subsequent to the nano-structured trampoline and gas molecular exchange of energy. Sensor sensitivity may be controlled by the external thermal modulation used to energize the nano- structured trampoline matrix material. The gas molecular detection device and system show a linear dependence between gas molecular weight and wavelength shift with 0.025 kg/kmol.pm sensitivity.

The fiber Bragg grating (FBG) based sensing device utilizes the nano-structured trampoline matrix layer as smart skin to detect gas molecular and its molar weight. External thermal modulation is used for matrix thermal tensile strain control, resulting in a structure that is highly sensitive to gas molecular detection. Using high coefficient of thermal expansion materials, the cool-down or thermal energy loss in the nano-structured trampoline matrix layer simultaneously induces a compressive thermal strain, surrounding the fiber Bragg grating cladding. Such a thermal strain in the nano-structure trampoline layer is detected by fiber Bragg grating's resonant wavelength shift. Experiment has shown that thermal energy loss by gas molecular absorption from nano-structured trampoline matrix layer depends on gas effective molecular molar weight.

This written description uses examples to disclose the invention, including the best mode, and also to enable any person skilled in the art to practice the invention with fiber gratings, thermocouples, thermometers and strain gauges, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fiber gas sensor comprising:
a core fiber comprising at least one fiber Bragg grating defining at least one fiber Bragg grating region, an outer surface and a length;
a fiber cladding in contact with the core fiber along the entire length of the core fiber, the fiber cladding having an outer surface and a length; and
a sensing matrix structure disposed upon the outer surface of the fiber cladding along a portion of the entire length of the fiber cladding and surrounding the fiber Bragg grating region, the sensing matrix structure comprising a nano-structured trampoline matrix layer comprising a material having a high-coefficient of thermal expansion and a high thermal conductivity,
wherein the sensing matrix structure is further comprised of a bonding layer and a capping layer, the bonding layer being disposed on an outer surface of the fiber cladding, the nano-structured trampoline matrix layer being disposed on an outer surface of the bonding layer, and the capping layer being disposed on an outer surface of the nano-structured trampoline matrix layer.

2. The fiber gas sensor as claimed in claim 1, wherein the core fiber comprises a plurality of Bragg grating regions.

3. The fiber gas sensor as claimed in claim 1, wherein the core fiber comprises at least one selected from the group consisting of silica, silicate glass, germanium doped silica, fluorine doped silica, silica doped with germanium oxide and fluorine.

4. The fiber gas sensor as claimed in claim 1, wherein the Bragg grating region has a length of about 2 to about 50 times the length of the Bragg grating.

5. The fiber gas sensor as claimed in claim 1, wherein the fiber cladding is at least one selected from the group consisting of a silica, a fluorine doped silica, a chlorine doped silica.

6. The fiber gas sensor as claimed in claim 1, wherein the nano-structured trampoline matrix layer comprises at least one of palladium (Pd), zinc (Zn), aluminum (Al), cobalt (Co), gold (Au), copper (Cu) and their alloys.

7. The fiber gas sensor as claimed in claim 6, wherein the nano-structured trampoline matrix layer has a thickness of about 1.0 micron to about 20microns.

8. The fiber gas sensor as claimed in claim 1, wherein the bonding layer comprises one of a titanium (Ti) based material or a titanium oxide based material.

9. The fiber gas sensor as claimed in claim 8, wherein bonding layer has a thickness of about 0.03 micron to about 0.1 micron.

10. The fiber gas sensor as claimed in claim 1, wherein the capping layer comprises an anti-corrosion and oxidization material.

11. The fiber gas sensor as claimed in claim 10, wherein capping layer has a thickness of about 0.05 micron to about 0.2 micron.

12. A fiber gas sensor comprising:
a core fiber comprising at least one Bragg grating defining at least one fiber Bragg grating region, an outer surface and a length;
a fiber cladding in contact with the core fiber along the entire length of the core fiber, the fiber cladding having an outer surface and a length; and
a sensing matrix structure disposed upon the outer surface of the fiber cladding along a portion of the entire length of the fiber cladding and surrounding the fiber Bragg grating region, the sensing matrix structure comprising:
a bonding layer disposed on the outer surface of the fiber cladding, the bonding layer having an outer surface and a length;
a nano-structured trampoline matrix layer comprising a material having a high-coefficient of thermal expansion and a high thermal conductivity disposed on the outer surface of the bonding layer, the nano-structured trampoline matrix layer having an outer surface and a length; and
a capping layer disposed on the outer surface of the nano-structured trampoline matrix layer, the capping layer having an outer surface and a length.

13. The fiber gas sensor as claimed in claim 12, wherein the nano-structured trampoline matrix layer comprises at least one of palladium (Pd), zinc (Zn), aluminum (Al), cobalt (Co), gold (Au) and copper (Cu) having a thickness of about 1.0micron to about 20 micron.

14. The fiber gas sensor as claimed in claim 12, wherein the bonding layer comprises one of titanium (Ti) based material or a titanium oxide based material having a thickness of about 0.03 micron to about 0.1 micron.

15. The fiber gas sensor as claimed in claim 12, wherein the capping layer comprises an anti-corrosion and oxidization material having a thickness of about 0.05 micron to about 0.2 micron.

16. A component for a fiber gas sensor comprising:
a core fiber comprising at least one fiber Bragg grating defining at least one fiber Bragg grating region, an outer surface and a length;
a fiber cladding in contact with the core fiber along the entire length of the core fiber, the fiber cladding having an outer surface and a length; and
a sensing matrix structure disposed upon the outer surface of the fiber cladding along a portion of the entire length of the fiber cladding and surrounding the at least one fiber Bragg grating region, the sensing matrix structure comprising:
a bonding layer disposed on the outer surface of the fiber cladding, the bonding layer having an outer surface and a length;
a nano-structured trampoline matrix layer comprising a material having a high-coefficient of thermal expansion and a high thermal conductivity material disposed on the outer surface of the bonding layer and comprising at least one of palladium (Pd), zinc (Zn), aluminum (Al), cobalt (Co), gold (Au) and copper (Cu), the matrix layer having an outer surface and a length; and
a capping layer disposed on the outer surface of the nano-structured trampoline matrix layer, the capping layer having an outer surface and a length.

17. The component for a fiber gas sensor as claimed in claim 16, wherein the nano-structured trampoline matrix layer has a thickness of about 1.0 micron to about 20 micron.

18. The component for a fiber gas sensor as claimed in claim 16, wherein the bonding layer comprises a titanium (Ti) based material or a titanium oxide based material having a thickness of about 0.03 micron to about 0.2 micron.

19. The component for a fiber gas sensor as claimed in claim 16, wherein the capping layer comprises an anti-corrosion and oxidization material having a thickness of about 0.05 micron to about 0.1 micron.

* * * * *